United States Patent
Samuels

(12) 
(10) Patent No.: US 6,375,006 B1
(45) Date of Patent: *Apr. 23, 2002

(54) METHOD AND APPARATUS FOR STORING MEDICAL GUIDEWIRES

(76) Inventor: Shaun Lawrence Wilkie Samuels, 1055 Sonoma Ave., Menlo Park, CA (US) 84025

( * ) Notice: Subject to any disclaimer, the term of this patent is extended or adjusted under 35 U.S.C. 154(b) by 0 days.

This patent is subject to a terminal disclaimer.

(21) Appl. No.: 09/545,953

(22) Filed: Apr. 10, 2000

Related U.S. Application Data

(63) Continuation-in-part of application No. 09/138,028, filed on Aug. 21, 1998, now Pat. No. 6,047,825.

(51) Int. Cl.[7] .............................................. B65D 83/10
(52) U.S. Cl. ........................ 206/364; 206/438; 206/210
(58) Field of Search ................................. 206/363, 438, 206/210, 364, 388, 225, 227; 220/661; 248/74.1, 74.2, 74.3; 604/93; 600/585, 434; 128/847

(56) References Cited

U.S. PATENT DOCUMENTS

| | | | | |
|---|---|---|---|---|
| 4,017,046 A | * | 4/1977 | Hicks .......................... | 248/74.1 |
| 4,193,699 A | * | 3/1980 | Haygeman et al. .......... | 206/373 |
| 4,607,746 A | | 8/1986 | Stinnette | |
| 5,102,399 A | * | 4/1992 | Chu ............................. | 604/250 |
| 5,125,416 A | * | 6/1992 | Phillips ....................... | 206/409 |
| 5,323,992 A | * | 6/1994 | Sifers et al. .............. | 248/205.3 |
| 5,507,300 A | * | 4/1996 | Mukai et al. ................ | 128/772 |
| 5,611,428 A | * | 3/1997 | Banerian ..................... | 206/364 |
| 5,720,301 A | * | 2/1998 | Van't Hooft ................. | 604/94 |
| 5,910,289 A | * | 6/1999 | Sagstetter .................... | 128/763 |
| 6,010,480 A | * | 1/2000 | Abele et al. ................. | 604/96 |
| 6,023,915 A | * | 2/2000 | Colombo ..................... | 206/204 |
| 6,047,825 A | * | 4/2000 | Samuels ...................... | 206/364 |
| 6,182,930 B1 | * | 2/2001 | Lindborg .................... | 248/74.1 |

* cited by examiner

*Primary Examiner*—Shzan Luong
(74) *Attorney, Agent, or Firm*—Piper Marbury Rudnick & Wolfe; R. Blake Johnston

(57) ABSTRACT

A flexible pipe features an open end and a generally closed end. The open end is elevated so that it is maintained above the remaining portion of the flexible pipe. The generally closed end of the pipe features a venting arrangement. As a result, the flexible pipe may be filled with fluid. The open end of the flexible pipe is flared and features dividers so that the ends of guidewires placed within the flexible pipe are separated. The flexible pipe features a cross section that prevents the guidewires stored therein from interacting with one another. The flexible pipe may be held in a coiled configuration by clamps. Alternatively, the flexible pipe may be straightened and attached to a surface, such as the sterile drapes covering a patient, by way of one or more wire/catheter guides which include channels positioned upon a base which features adhesive. A wire gutter serves as a bridge between the flexible pipe and the patient and features adhesive so that is may be attached to the drapes covering the patient.

20 Claims, 7 Drawing Sheets

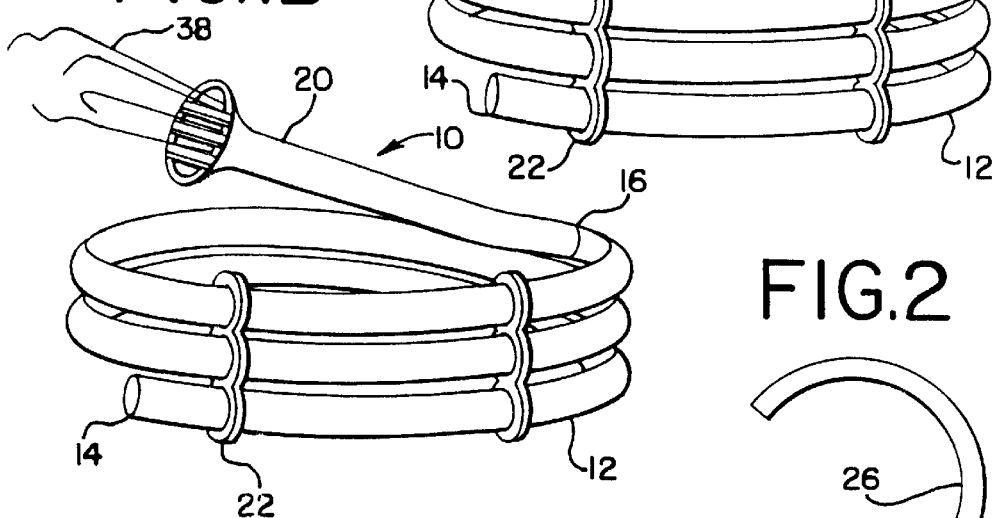
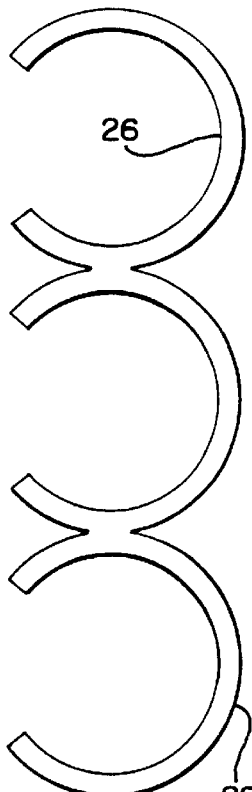
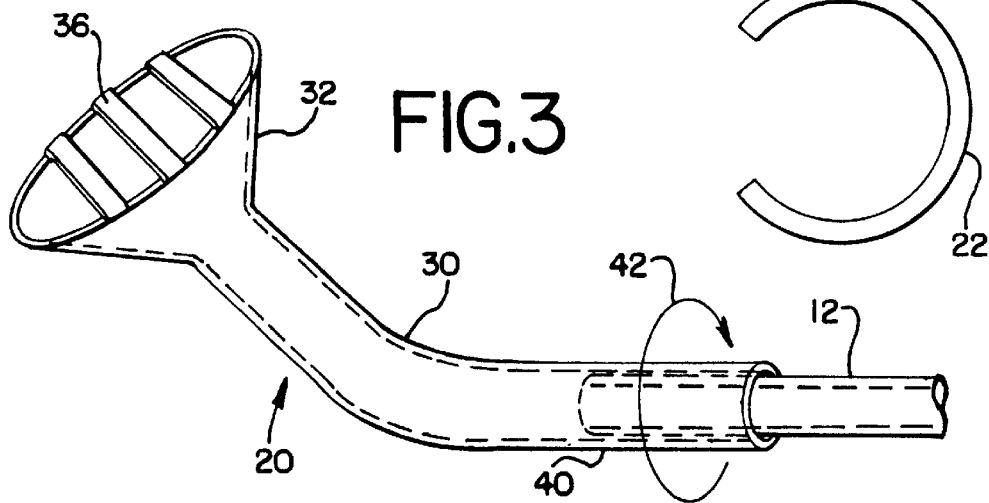

METHOD AND APPARATUS FOR STORING MEDICAL GUIDEWIRES

This application is a continuation-in-part of U.S. application Ser. No. 09/138,028 filed Aug. 21, 1998.

BACKGROUND OF THE INVENTION

A number of interventional radiologic medical techniques have been recently developed to address a variety of potentially life-threatening human ailments. For example, interventional radiologic techniques have been developed to allow removal and/or destruction of stones in the biliary or excretory systems, blood clots in blood vessels and foreign bodies introduced by surgery that have migrated or become dysfunctional. As another example, interventional radiologic techniques may be utilized to treat stenosis, a degenerative blood vessel condition that causes a narrowing or constriction of the lumen so that blood flow is restricted. Due to their minimally invasive nature, interventional radiologic techniques provide an attractive alternative to surgery and thus have become very popular.

Interventional radiologic techniques typically utilize a wire that passes from outside of the patient's body, through his or her skin and into the tubular structure of interest. Once the wire is positioned in the desired location, medical devices, such as catheters, may be passed over the wire and thereby guided into the tubular structure so that the desired medical procedure may be performed. These "guidewires", as they have come to be called, are of various lengths, calibers and materials, depending on the use for which they are intended.

In use, guidewires, after removal from their sterile packaging, are inserted into the patient and the portion remaining outside of the patient's body is spooled by hand, as would be an extension cord. More specifically, the external portion of a guidewire is wound about itself in such a way as to "lock" the wire from springing into its naturally straight configuration. The wound portion of the guidewire is then placed into a large bowl containing a sterile saline solution so as to keep the wire wet. The saline solution also promotes the dissolution of any clots which may have formed on the guidewire after it is removed from the patient and placed in the bowl.

Oftentimes several different guidewires may be used during a single procedure. As a result, a number of wound guidewire portions may accumulate in a bowl. In addition, several catheters may be placed in the bowl. It thus often becomes difficult for a physician to locate a specific guidewire within the bowl during a procedure.

Wound guidewires also have a tendency to straighten once unlocked. As a result, a guidewire may spring open unexpectedly when it is being unwound during a procedure. When this occurs, the guidewire may inadvertently come into contact with non-sterile areas of the procedure room, and hence need to be resterilized or completely replaced.

The bowls containing the wound guidewire portions and catheters may also be accidently tipped over during procedures. Such a scenario would also likely result in the catheters and guidewires coming into to contact with non-sterile areas of the procedure room such as the floor.

Accordingly, it is an object of the present invention to provide a method and apparatus for storing medical guidewires that maintains them submersed in liquid.

It is another object of the present invention to provide a method and apparatus for storing multiple medical guidewires of various sizes and types so that they are organized for easy identification and access.

It is another object of the present invention to provide a method and apparatus for storing medical guidewires that allows for their easy introduction into a patient and removal therefrom.

It is still another object of the present invention to provide a method and apparatus for storing medical guidewires so that they don't spring open unexpectedly during a procedure.

It is still another object of the present invention to provide a method and apparatus for storing medical guidewires that prevents their contact with non-sterile portions of the procedure room.

SUMMARY OF THE INVENTION

The present invention is directed to a method and apparatus for storing medical guidewires. The apparatus features a flexible, hollow pipe having a generally closed end and an open end. A nozzle is disposed at the open end of the flexible pipe by a friction joint. As a result, the nozzle may be removed or repositioned. The nozzle features an elbow portion so that the opening of the nozzle is elevated above the flexible pipe. Alternatively, the open end of the flexible pipe is elevated by a collar or stand. This allows fluid to be retained in the flexible pipe. The generally closed end of the pipe is provided with a venting arrangement to facilitate the filling of the pipe with the fluid.

The nozzle or open end is flared and features a number of dividers. These dividers support and organize the guidewires that have been placed within the flexible pipe for easy access by the physician. The flexible pipe may feature a variety of cross sections to prevent interaction of the guidewires stored therein. The flexible pipe may contain a wiping plate formed of gauze or the like with slits aligned with the dividers so that the guidewires may be automatically wiped.

The flexible pipe may be secured in a coiled configuration with one or more clamps. Alternatively, the flexible pipe may be uncoiled and attached to a surface, such as the sterile drapes covering a patient, using one or more wire/catheter guides. The wire/catheter guides feature stacked channels positioned upon a base. The base features adhesive so the wire/catheter guide may be attached to the surface of interest. The channels are sized to accommodate the flexible pipe and feature longitudinal grooves or openings. As a result, the flexible pipe may be inserted into one or more of the channels. One possible arrangement is to locate the flexible pipe in one channel while using the other channel to guide catheters or guidewires that are not stored within the flexible pipe.

A wire gutter featuring an arc-shaped cross section serves as a bridge between the flexible pipe and the patient. The wire gutter is provided with adhesive so that it may be attached to the drapes covering a patient. The wire gutter may feature a variety of alternative cross sections and fastening arrangements.

BRIEF DESCRIPTION OF THE DRAWINGS

FIGS. 1A and 1B are perspective views of an embodiment of the apparatus for storing medical guidewires of the present invention in a coiled configuration without and with medical guidewires inserted therein, respectively;

FIG. 2 is an enlarged end elevation view of the clamp of the apparatus of FIGS. 1A and 1B;

FIG. 3 is an enlarged perspective view of the nozzle of the apparatus of FIGS. 1A and 1B;

DESCRIPTION OF THE PREFERRED EMBODIMENTS

Figure 4:
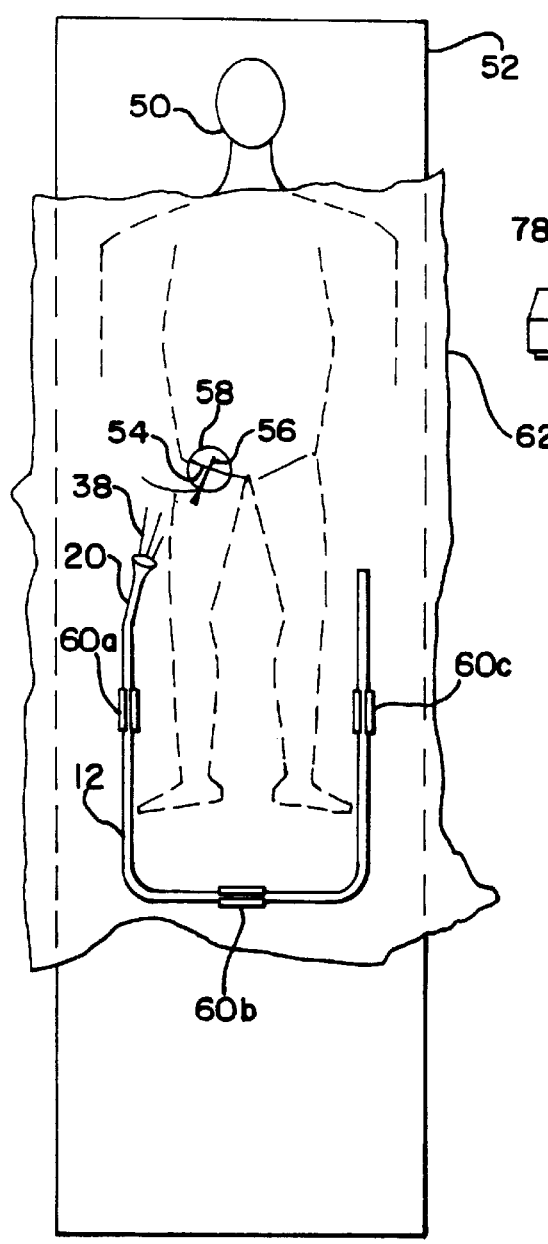
FIG. 4 is a top plan view of the apparatus of FIGS. 1A and 1B utilizing wire/catheter guides during a medical procedure.

Referring to FIGS. 1A and 1B, an embodiment of the apparatus of the present invention, in a coiled configuration, is indicated generally at 10. The apparatus 10 features a flexible pipe 12 that is sealed on one end 14. The open end 16 is fitted with a nozzle 20. A number of clamps 22 are attached to flexible pipe 12 so as to hold it in the coiled configuration. Flexible pipe 12, clamps 22 and nozzle 20 are preferably made of flexible polymeric plastic. While the embodiment shown in FIGS. 1A and 1B shows the nozzle 20 as a separate piece that is attached to flexible pipe 12, it is to be understood that the flexible pipe and nozzle could be manufactured as a single, integral piece.

As shown in FIG. 2, clamp 22 features a number of interconnected "C-shaped" sections. The innersurface 26 of each C-shaped section defines a generally circular area that is slightly smaller than the cross section defined by the outer surface of flexible pipe 12. As a result, flexible pipe 12 may be inserted into, and secured within, clamp 22. It is to be noted that while three such C-shaped sections are shown in FIG. 2, clamp 22 may incorporate any number of such sections so that the flexible pipe 12 of the device (FIGS. 1A and 1B) may be wound into more or less than three coils.

As shown in FIG. 3, the nozzle 20 of the device preferably features an elbow portion 30 and a flared portion 32. Flared portion 32 features an enlarged opening, the latter of which is spanned by dividers 36. Dividers 36 are essentially strips of plastic that are attached by their ends to the interior of the flared portion 32 of nozzle 20. The enlarged opening and dividers 36 allow a multitude of guidewires 38 to be inserted into the device while keeping them separated and organized, as illustrated in FIG. 1B. As a result, the physician is better able to select the proper guidewire during a procedure. It is to be noted that the configuration of the dividers 36 shown is an example only. The dividers or grating across the opening could take on a number of configurations including, for example, a crossed arrangement.

Elbow portion 30 maintains flared portion 32 in an elevated state so that liquid, such as sterile saline solution, may be retained within flexible pipe 12. This allows the guidewires 38 to remain primarily submersed in the fluid.

Nozzle 20 is preferably attached to an end of flexible pipe 12 via a friction joint 40. More specifically, the cross-sectional area defined by the inner surface of the non-flared portion of nozzle 20 is slightly smaller than the cross-sectional area defined by the outer surface of flexible pipe 12. As a result, nozzle 20 and flexible pipe 12 are joined in an interference-fit fashion so that liquid will not leak out. In addition, friction joint 40 allows nozzle 30 to be rotated about flexible pipe 12 through 360°, as illustrated by arrow 42, to allow for adjustment and positioning of flexible pipe 12 without the removal of the liquid or guidewires therein. Friction joint 40 also allows nozzle 20 to be removed so that guidewires inadvertently placed beyond the enlarged opening and dividers 36 may be easily retrieved from flexible pipe 12.

As stated previously, clamps 22 (FIGS. 1A and 1B) are easily removable from flexible pipe 12 so that the latter may be straightened or placed in a more convenient configuration. For example, the flexible pipe 12 may be placed in a configuration roughly outlining a patient 50 laying on a procedure table 52, as illustrated in FIG. 4. As shown in FIG. 4, the flexible pipe 12 is held in place on the sterile drapes 62 covering the patient 50 by way of wire/catheter guides 60a, 60b and 60c. With flexible pipe 12 so positioned, the physician may select the guidewires 38 to be inserted into the patient through access site 54.

Access site 54 is an incision in the patient's skin that leads to the tubular structure of interest within the patient's body. As is known in the art, a sheath 56 is inserted through the site 54 so that guidewires 38 may be introduced into the tubular structure. An opening 58 in sterile drape 62 allows the physician to access sheath 56.

When in an uncoiled arrangement, such as the one illustrated in FIG. 4, the flexible pipe 12 offers less resistance to the movement of the guidewires 38 stored therein. As a result, the physician may more easily withdraw guidewires 38 from flexible pipe 12, and feed guidewires 38 into flexible pipe 12, during a procedure. Oftentimes the withdrawal and feeding of guidewires 38 may even be accomplished by a physician using just one hand. This leaves the physician's other hand free for use during more complicated procedures.

Figure 5:
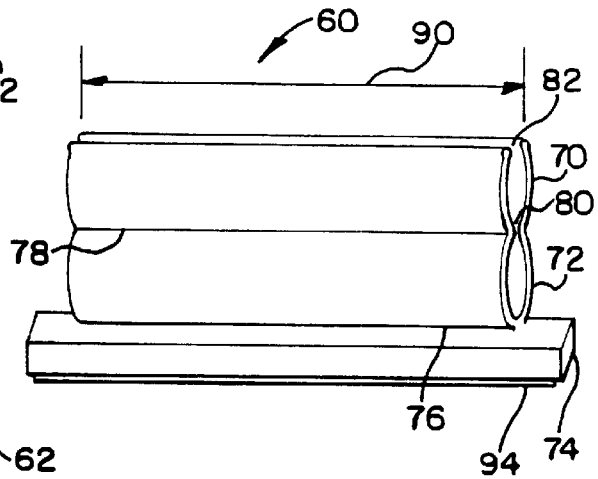
FIG. 5 is an enlarged perspective view of one of the wire/catheter guides of FIG. 4.
Figure 6:
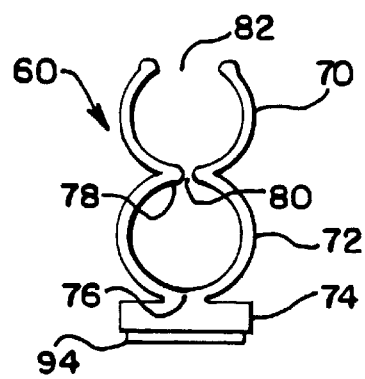
FIG. 6 is an end elevation view of the wire/catheter guide of FIG. 5.

Referring to FIGS. 5 and 6, each wire/catheter guide 60 features an upper channel 70 and a lower channel 72 positioned upon a base 74. However, wire/catheter guide 60 may be constructed with any number of channels, including only one. The lower channel 72 is attached by its bottom surface 76 to base 74. The junction 78 between lower channel 72 and upper channel 70 features a longitudinal groove 80 while the upper channel 70 features a longitudinal opening 82.

Wire/catheter guide 60 is preferably constructed of flexible polymeric plastic and upper and lower channels 70 and 72 are sized so that flexible pipe 12 (FIG. 4) may be held snugly therein while still permitting some movement. The lengths of channels 70 and 72, indicated at 90 in FIG. 5, is preferably between 1 and 6 cm. Opening 82 is sized so that flexible pipe 12 may be snapped therethrough and into upper channel 70. Similarly, groove 80 allows flexible pipe 12 to be pressed therethrough and into lower channel 72.

By providing a pair of channels 70 and 72, wire/catheter guide 60 may accommodate two flexible pipes 12. Furthermore, it is possible to use one of the channels 70 or 72 to accommodate flexible pipe 12 while the other is used to guide catheters or guidewires that are not stored within flexible pipe 12. The wire/catheter guide 60 may also be used independently of flexible pipe 12 to guide catheters and guidewires.

The bottom 92 of base 74 features an adhesive 94. As a result, the wire/catheter guide may be positioned in a number of locations including, for example, on the sterile drapes covering the patient (as shown in FIG. 4) or on the procedure table itself.

Figure 7:
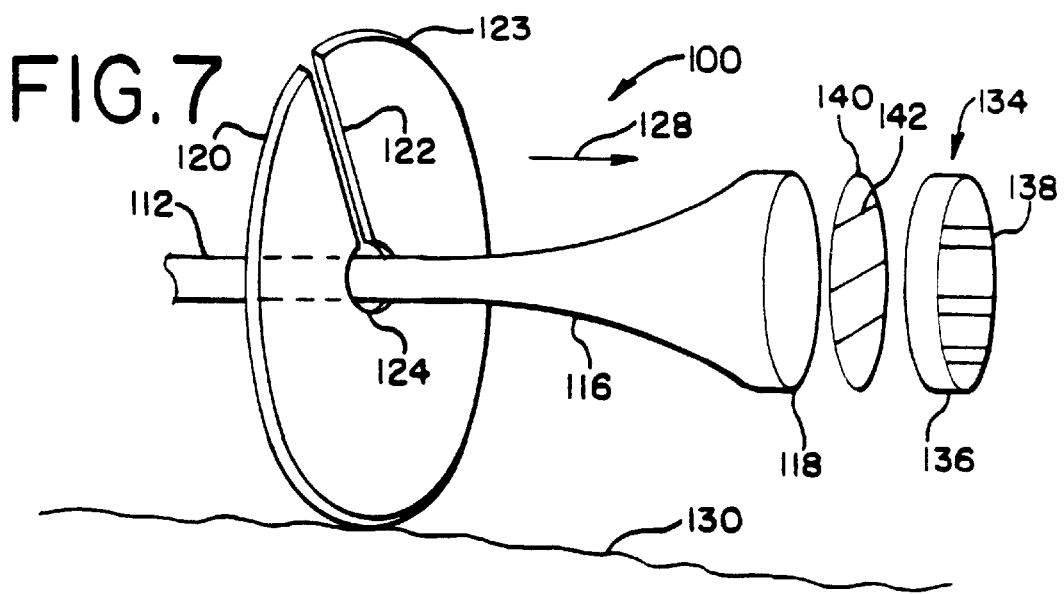
FIG. 7 is a partial perspective view of a second embodiment of the apparatus for storing medical guidewires of the present invention.

A second embodiment of the apparatus of the present invention is indicated generally at 100 in FIG. 7. Like the embodiment of FIGS. 1A and 1B, apparatus 100 features a flexible pipe 112 with a sealed end (not shown). In contrast to the embodiment of FIGS. 1A and 1B, however, apparatus 100 does not feature a nozzle that is separable from the flexible pipe 112. Flexible pipe 112 features a flared portion 116 that terminates into, or is adjacent to, open end 118.

An elevating collar 120, preferably formed of thin plastic, features a radial groove 122 extending from the edge 123 of the collar to a central aperture 124. As a result, flexible pipe 112 may be passed through radial groove 122 so that the flexible pipe is positioned through central aperture 124 (as shown in FIG. 7). Elevating collar may then be slid in the direction of arrow 128 until central aperture 124 grips the surface of flared portion 116. When so positioned, elevating collar 120 operates to maintain open end 118 in an elevated position with respect to the remaining portion of flexible pipe 112 and a surface 130. As a result, liquid, such as sterile saline solution, may be retained within flexible pipe 112. It should be noted that elevating collar 120 may feature a shape other than that of a disk.

A divider cap, indicated generally at 134, is sized so as to removably engage flexible pipe 112 so as to cover open end 118. As shown in FIG. 7, divider cap 134 features a rim 136 across which a number of dividers 138 are positioned. Dividers 138 are essentially thin strips of material formed across rim 136. When placed over open end 118, the dividers 138 are capable of supporting a number of guidewires in a spaced and organized fashion for easy access by the physician. Divider cap 134 is preferably made from plastic. It should be noted that the configuration shown for dividers 138 is an example only and that a variety of other grating arrangements (such as crossed dividers) are possible.

A wiping plate, indicated at 140 in FIG. 7, is sized so that it may be positioned within flexible pipe 112, just barely inside open end 118. Wiping plate 140 is preferably made of gauze or a similar material such as TEFLA. Wiping plate 140 is provided with a number of slits 142 positioned so as to be aligned with the top edges of dividers 138 (or whatever divider configuration is utilized). The inclusion of wiping plate 140 allows guidewires to be automatically wiped upon introduction into and withdrawal from flexible pipe 112. Divider cap 134 may be removed from flexible pipe 112 to allow removal or insertion of wiping plate 140.

Figure 8:
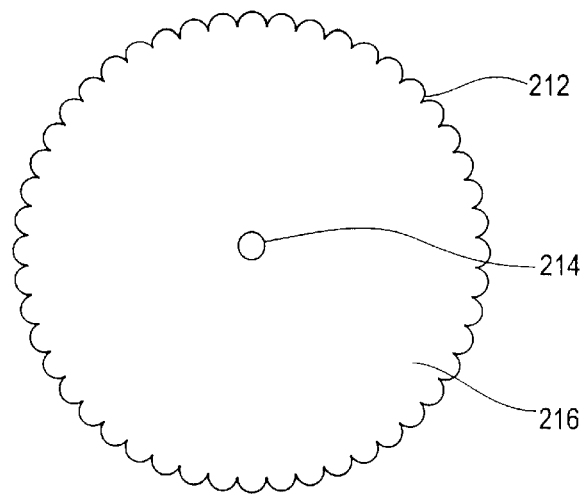
FIG. 8 is a cross section view of the flexible pipe of a third embodiment of the apparatus for storing medical guidewires of the present invention.

While the embodiments of the invention illustrated in FIGS. 1–7 feature flexible pipes with round cross sections, other cross sections are possible. Such cross sections may include partitions protruding into the interior space of the flexible pipe. For example, as illustrated in FIG. 8, the flexible pipe 212 may feature a corrugated construction with the corrugations serving as the partitions and running along the entire length of the flexible pipe, or a portion thereof, and generally parallel to the longitudinal axis 214 of the pipe. As a result, guidewires placed within the interior space 216 defined by the flexible pipe 212 tend to fall within corrugations that are not occupied by other guidewires. Guidewires placed within interior space 216 thus tend to be separated so as to prevent interaction with one another. This provides a physician ease of insertion, access and use of the guidewires positioned in the pipe.

Figure 9:
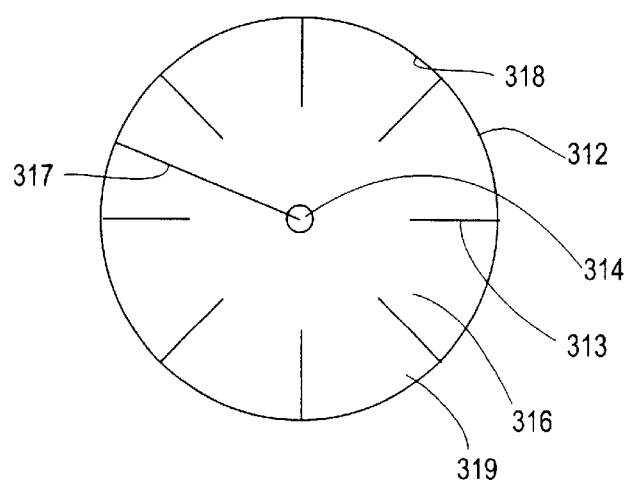
FIG. 9 is a cross section view of the flexible pipe of a fourth embodiment of the apparatus for storing medical guidewires of the present invention.

As illustrated by flexible pipe 312 in FIG. 9, a number of walls 313 may alternatively be positioned upon the interior surface 318 of the pipe so as to extend into the interior space 316 in a radial fashion. The walls may be spaced equal distance from one another along the pipe interior surface as shown. Each wall features a height that is less than the radius 317 of the flexible pipe 312. The walls 313 span the entire pipe length, or a portion thereof, in an orientation parallel to the longitudinal axis 314 of the pipe so that troughs 319 are defined. Medical guidewires inserted within the flexible pipe may be positioned in separate troughs 319 to prevent their interaction with one another.

Figure 10:
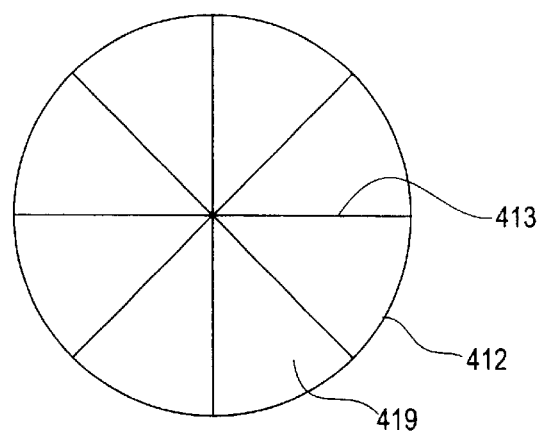
FIG. 10 is a cross section view of the flexible pipe of a fifth embodiment of the apparatus for storing medical guidewires of the present invention.

As illustrated in FIG. 10, a flexible pipe 412 may alternatively be provided where the interior space defined thereby is divided into pie-shaped 419 sections by cross members 413. Cross members 413 extend across the diameter of the flexible pipe so as to intersect at the longitudinal axis of the pipe. The cross members may extend along the entire length of the pipe 412, or a portion thereof. Guidewires may be positioned in separate sections 419 to prevent their interaction with one another.

It should be noted that cross sections other than the ones illustrated in FIGS. 8–10 may alternatively be employed for separating the guidewires placed within the pipe.

Figure 11:
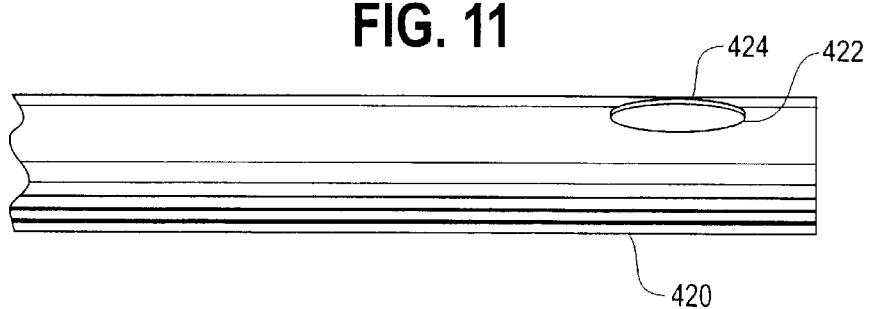
FIG. 11 is a perspective view of an end portion of the flexible pipe of an embodiment of the apparatus for storing medical guidewires of the present invention featuring an air permeable and water impermeable vent.

In order to facilitate filling of the flexible pipe of the present invention with liquid, the generally closed end of the flexible pipe, indicated at 14 in FIG. 1, may optionally be provided with an air vent. Such a vent permits the escape of gas that is displaced, and potentially trapped, by liquid if the pipe is rapidly filled. As illustrated in FIG. 11, where the generally closed end portion 420 of a flexible pipe is shown, the vent may take the form of an opening 422 that is covered with a sheet of gas permeable, but liquid impermeable, material 424. Such material may be, for example, polyester mesh or plastic mesh. The material may be fastened to the interior surface of the pipe that surrounds the opening by a suitable adhesive. Alternative fastening arrangements may also be employed.

Figure 12A:
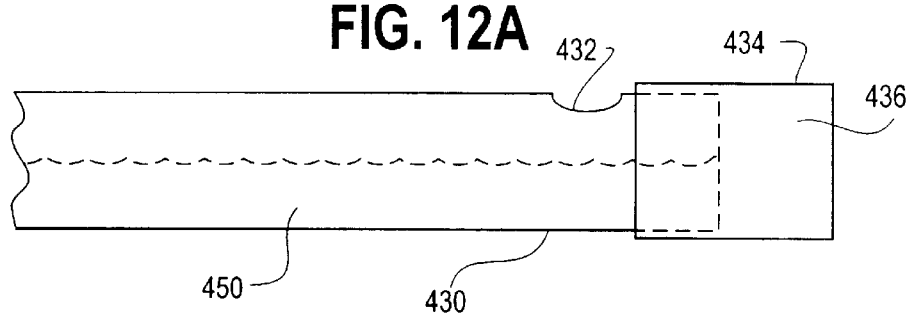
FIGS. 12A and 12B are side elevation views of an end portion of the flexible pipe of an embodiment of the apparatus for storing medical guidewires of the present invention featuring a closable vent illustrating open and closed configurations, respectively.
Figure 12B:
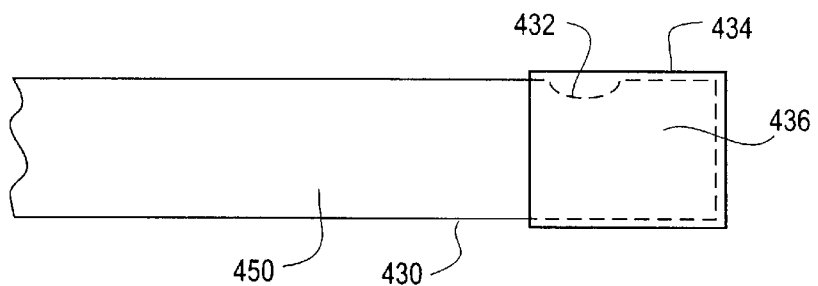

An alternative vent arrangement is illustrated in FIGS. 12A and 12B. A generally closed end portion of a flexible pipe is illustrated at 430 wherein an opening 432 is formed. A cap 434 features an interior chamber 436 that is sized large enough to slide upon the exterior surface of pipe yet is small enough to form a seal about opening 432 when the cap is in the "closed" position illustrated in FIG. 12B. As a result, liquid 450 may easily be added to the flexible pipe when the cap is in the "open" position illustrated in FIG. 12A as the opening 432 permits air that is displaced to escape. When the liquid level in the pipe begins to reach a level where the pipe is filled, the cap 434 may be configured in the "closed"

position, illustrated in FIG. 12B, so that the opening 432 is sealed. As a result, liquid does not flow out of opening 432.

Alternative air venting arrangements known in the art may be substituted for the vents illustrated in FIGS. 11, 12A and 12B. Such venting arrangements could include, for example, valves.

Figure 13:
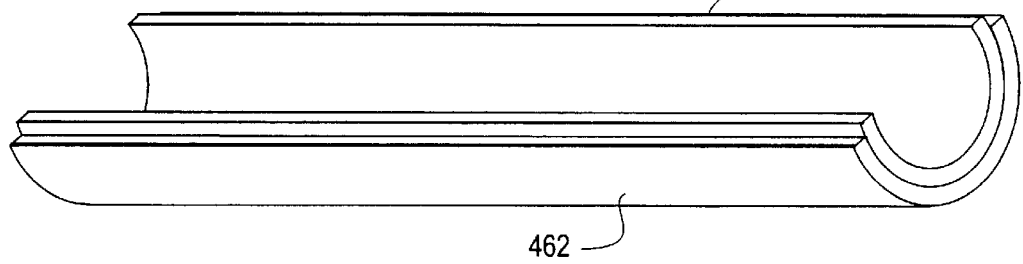
FIG. 13 is a perspective view of a wire gutter of an embodiment of the apparatus for storing medical guidewires of the present invention.
Figure 14:
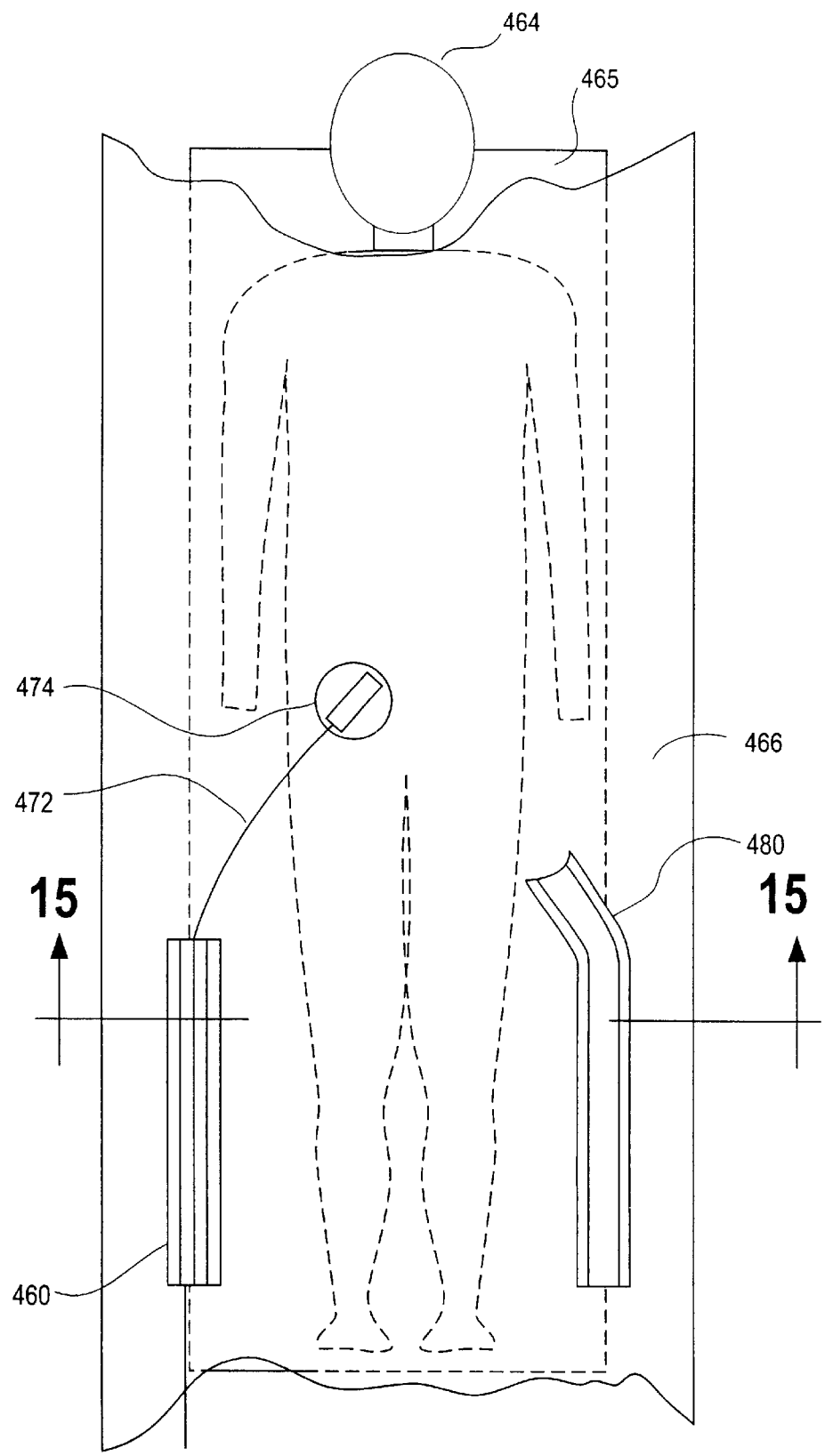
FIG. 14 is a top plan view illustrating use of the wire gutter of FIG. 13 during a medical procedure.
Figure 15:
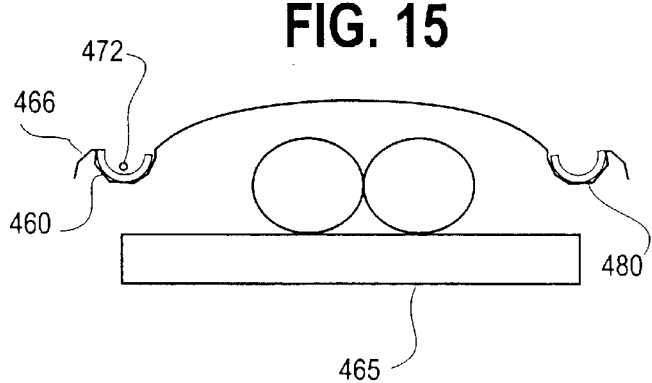
FIG. 15 is a cross section view of the wire gutters, angio table, patient and drapes of FIG. 14 taken along line 15—15.
Figure 16:
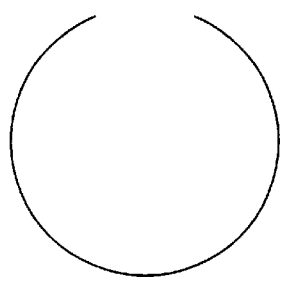
FIGS. 16–20 are cross section views of alternative embodiments of the wire gutter of the apparatus for storing medical guidewires of the present invention.
Figure 17:
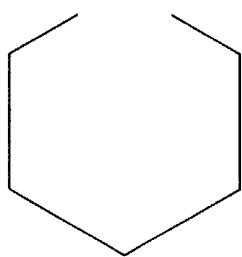
Figure 18:
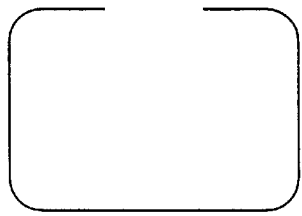

A wire gutter, illustrated at 460 in FIG. 13, may be utilized with the flexible pipe of the present invention to facilitate guidance of medical guidewires between the flexible pipe and a patient 464 positioned upon an operating table 465. As illustrated in FIG. 13, the gutter 460 features an arc-shaped cross section (see also FIG. 15) with adhesive 462 secured to its lower surface. The adhesive allows the gutter to be attached to a surface such as the drapes 466 covering a patient, as illustrated in FIGS. 14 and 15. Clips, magnets, hooks, pins or velcro could be secured to the wire gutter 460 in place of adhesive 462 to provide an alternative fashioning arrangement.

As illustrated in FIGS. 14 and 15, a guidewire 472 is fed from a flexible pipe, such as the one illustrated in FIGS. 1A and 1B (but not shown in FIGS. 14 and 15), through wire gutter 460 and into the patient's puncture site 474 (FIG. 14). As such, wire gutter 460 serves as a bridge between the flexible pipe and the patient. In doing so, the wire gutter prevents the guidewires from falling on the operating room floor and assists the physician in positioning the guidewires within the patient. It should be noted that the wire gutter 460 may be used by itself, that is, without the flexible pipe, to accomplish these functions. As illustrated by wire gutter 480 in FIG. 14, the wire gutter of the present invention may optionally be curved or bent towards the center of the operating room table so as to direct guidewires placed therein towards the patient.

Figure 19:
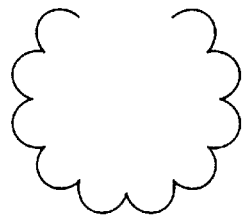
Figure 20:
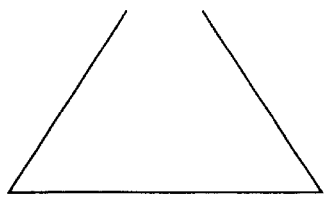

While the wire gutters 460 and 480 feature arc-shaped cross sections, as illustrated in FIG. 15, a variety of alternative cross sectional shapes may be utilized. For example, wire gutters constructed in accordance with the present invention may have the cross sections illustrated in FIGS. 16–20. These cross sections aid in the retention of guidewires placed within the gutter. In addition, guidewires placed within the corrugated wire gutter of FIG. 19 tend to be separated so that they don't interact with one another.

While the preferred embodiments of the invention have been shown and described, it will be apparent to those skilled in the art that changes and modifications may be made therein without departing from the spirit of the invention, the scope of which is defined by the appended claims.

What is claimed is:

1. An apparatus for storing medical guidewires comprising:
    a) a flexible pipe capable of being turned or coiled, said flexible pipe having a first end and a closed second end;
    b) said first end of said flexible pipe featuring an opening through which the guidewires may be inserted into said flexible pipe and removed from said flexible pipe; and
    c) said second end of said flexible pipe featuring a vent sized to facilitate the introduction of liquid into said flexible pipe through the opening by permitting air in the pipe displaced by the introduced liquid to escape through the vent.

2. The apparatus of claim 1 wherein said vent includes an opening in the flexible pipe positioned proximate to the second end of the flexible pipe with the opening covered by a gas permeable but liquid impermeable material.

3. The apparatus of claim 1 wherein said vent includes an opening in the flexible pipe positioned proximate to the second end of the flexible pipe and a cylindrical cap slidably mounted upon the second end of the flexible pipe so that said cap may slide between an open position whereby the opening is uncovered while the cap is still slidably mounted upon the pipe and a closed position whereby the opening is covered in a generally sealed fashion.

4. The apparatus of claim 1 wherein said flexible pipe includes means for separating guidewires positioned therein.

5. The apparatus of claim 4 wherein said means for separating guidewires includes corrugations formed in said flexible pipe, said corrugations running generally parallel to a longitudinal axis of the flexible pipe.

6. The apparatus of claim 4 wherein said means for separating guidewires includes a plurality of walls protruding into an interior space defined by the flexible pipe, said plurality of walls oriented generally parallel to a longitudinal axis of the flexible pipe.

7. The apparatus of claim 4 wherein said means for separating guidewires includes a cross member extending across an interior space defined by the flexible pipe, said cross member oriented generally parallel to a longitudinal axis of the flexible pipe.

8. The apparatus of claim 1 further comprising a clamp featuring a plurality of sections stacked upon top of one another, each section adapted to secure a portion of said flexible pipe so that said flexible pipe may be arranged in a coiled configuration.

9. The apparatus of claim 1 further comprising a nozzle portion in communication with the opening of the flexible pipe, said nozzle including an elbow portion so that said nozzle may be elevated above said flexible pipe so that fluid may be contained in said flexible pipe.

10. The apparatus of claim 1 further comprising a wire/catheter guide including a channel positioned upon a base, said channel sized to removably receive said flexible pipe and said base including means for mounting said wire/catheter guide to a surface.

11. The apparatus of claim 1 further comprising an elevating collar including a central aperture and a radial groove extending from the central aperture to the edge of the elevating collar, said central aperture sized to receive said flexible pipe after said flexible pipe is slid through said radial groove and said elevating collar sized to elevate the first end of the flexible pipe above a surface.

12. A system for storing medical guidewires and providing the medical guidewires to a patient during a medical procedure comprising:
    a) a flexible pipe capable of being turned or coiled, said flexible pipe having a first end and a closed second end;
    b) said first end of said flexible pipe featuring an opening through which the guidewires may be inserted into said flexible pipe and removed from said flexible pipe;
    c) said second end of said flexible pipe featuring a vent sized to facilitate the introduction of liquid into said flexible pipe through the opening by permitting air in the pipe displaced by the introduced liquid to escape through the vent;
    d) a wire gutter having an open top so that a plurality of the guidewires may be laid therein; and
    e) means for securing the wire gutter to a surface in a position between the flexible pipe and the patient so that guidewires positioned in the wire gutter are directed from the flexible pipe towards the patient.

13. The apparatus of claim 12 wherein said wire gutter includes means for separating guidewires positioned therein.

14. The apparatus of claim 12 wherein said wire gutter is curved.

15. The apparatus of claim 12 wherein said means for securing the wire gutter to a surface includes adhesive.

16. An apparatus for storing a plurality of medical guidewires comprising:
   a) a flexible pipe capable of being turned or coiled, said flexible pipe defining an interior space;
   b) said flexible pipe including a generally open end sized so that the plurality of medical guidewires may be inserted into and removed from the interior space;
   c) said flexible pipe including a closed second end featuring a vent sized to facilitate the introduction of liquid into the interior space through the open end by permitting air in the pipe displaced by the introduced liquid to escape through the vent; and
   d) partitions protruding into the interior space of the pipe so that the guidewires positioned therein may be separated from one another.

17. The apparatus of claim 16 wherein the partitions are corrugations.

18. The apparatus of claim 16 wherein the partitions are walls.

19. The apparatus of claim 16 wherein the partitions are crossmembers.

20. The apparatus of claim 16 further comprising a wire gutter sized to receive the plurality of the guidewires and means for securing the wire gutter to a surface positioned between the flexible pipe and a patient so that the plurality of guidewires are directed to the patient.

* * * * *